United States Patent [19]

Meek et al.

[11] Plant 4,492

[45] Jan. 8, 1980

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 925,970

[22] Filed: Jul. 18, 1978

[51] Int. Cl.[2] ..... A01H 5/00

[52] U.S. Cl. ..... Plt./74

[58] Field of Search ..... Plt./74

*Primary Examiner*—Robert E. Bagwill
*Attorney, Agent, or Firm*—Donald D. Jeffery

[57] ABSTRACT

A daisy capitulum type of chrysanthemum plant which is a sport of the cultivar Circus, disclosed in U.S. Plant Pat. No. 4,188. Cirbronze is distinguished from the parent cultivar by its medium bronze ray floret color.

1 Drawing Figure

The present invention comprises a new and distinct cultivar of *Chrysanthemum morifolium,* Ramat., hereinafter referred to by the cultivar name of Cirbronze.

Cirbronze is a product of planned sport induction program which had the objective of expanding the color range of the parental cultivar, Circus (U.S. Plant Pat. No. 4,188).

Cirbronze was discovered and selected by William E. Duffett and Jack M. Meek on Feb. 14, 1977 as one plant within a flowering block of Circus in a controlled environment in Barberton, Ohio. Plants within the flowering block were derived from stock plants which had been irradiated as rooted cuttings with an x-ray source of 2600 r units.

The first act of asexual reproduction of Cirbronze was accomplished when vegetative cuttings were taken from the initial selection in April, 1977 in a controlled environment in Barberton, Ohio by a technician working under formulations established and supervised by William E. Duffett and Jack M. Meek. Horticultural examination of selected units initiated Apr. 25, 1978 has demonstrated that the combination of characteristics as herein disclosed for Cirbronze are firmly fixed and are retained through successive generations of asexual reproduction.

Cirbronze has not been observed under all possible environmental conditions. The phenotype may vary significantly with variations in environment such as temperature, light intensity and daylength. The following observations, measurements, and comparisons describe plants grown in Salinas, Calif. under greenhouse environmental conditions which approximate those generally used in commercial practice.

The following traits have been repeatedly observed and are determined to be basic characteristics of Cirbronze which in combination distinguish this chrysanthemum as a new and distinct cultivar:

(1 ) Daisy capitulum type.
(2) Flat capitulum form.
(3) Medium bronze ray floret color.
(4 ) Diameter across face of inflorescence ranging from 55 to 75 mm. at maturity.
(5) Uniform nine week photoperiodic flowering response to short days.
(6) Medium plant height (requires 1 to 2 long day weeks prior to short days and one application 2500 ppm B-9 SP 14 to 21 days after the beginning of short days to attain a flowered plant height of 30 to 45 cm. when grown as a pinched pot for year round flowerings).
(7) Semi-spreading branching pattern.
(8) Yellow green (immature) to yellow (mature) disc floret color.

The accompanying color photographic drawing shows typical inflorescence and foliage characteristics of Cirbronze. Some difficulty was encountered in obtaining accurate color representation, the photographic rendition being more blue and less red than the actual flower color of Cirbronze. The color readings in the following description are, however, correct.

Of the many commercial cultivars known to the present inventors, the most similar existing cultivars in comparison to Cirbronze are the parental cultivar Circus and Dixie (U.S. Plant Pat. No. 3,655). Reference is made to attached Chart A which compares certain characteristics of Cirbronze with the same characteristics of Circus and Dixie. General comparisons are as follows:

(1.) In comparison to Circus, Cirbronze has different ray floret color, with all other characteristics being similar to those same characteristics of Circus.

(2) In comparison to Dixie, Cirbronze has less orange ray floret color, smaller diameter across face of capitulum, and taller plant height. The branching pattern, flowering response period, capitulum form, and capitulum type of Cirbronze are similar to those same characteristics of Dixie.

In the following description, color references are made to The Royal Horticultural Society Colour Chart. The color values for the foliage and reproductive organs were determined between 11:00 and 11:30 A.M. on June 8, 1978 under 200 foot-candle light intensity at Salinas, Calif. The color values for the inflorescence were determined between 10:30 and 11:00 A.M. on Jan. 29, 1979 under 100 foot-candle light intensity at Salinas, Calif.

BOTANICAL CLASSIFICATION: *Chrysanthemum morifolium,* Ramat., cv. Cirbronze

I. INFLORESCENCE

A. Capitulum:
*Form.*—Flat.
*Type.*—Daisy.
*Permanence.*—14 to 18 days.
*Diameter across face.*—55 to 75 mm.

B. Corolla of Ray Florets:

*Color (abaxial).*—168-A (immature) to 168-A streaked over 162-A (mature), oxidizing to 172-C streaked over 164-C.

*Color (adaxial).*—171-B to 165-B streaked over 162-A to 162-C.

C. Corolla of Disc Florets:

*Color (immature).*—144-A.

*Color (mature).*—17-C.

D. Reproductive Organs:

*Androecium.*—Present disc florets only; moderate pollen.

*Gynoecium.*—Present both ray and disc florets.

II. PLANT

A. General Appearance: Semi-spreading branching pattern; medium height.

B. Foliage:

*Color (abaxial).*—Approximately 139-A.

*Color (adaxial).*—Approximately 137-C overlaid with white.

CHART A

COMPARISON OF CIRBRONZE, CIRCUS AND DIXIE

| CULTIVAR | RAY FLORET COLOR | DIAMETER ACROSS FACE OF CAPITULUM | PLANT HEIGHT |
|---|---|---|---|
| Cirbronze | Medium bronze | 55 to 75 mm. | Medium, 30 to 45 cm. |
| Circus | Lavender pink | 57 to 70 mm. | Medium, 30 to 45 cm. |
| Dixie | Orange bronze | 80 to 100 mm. | Short, 25 to 40 cm. |

CHART A-continued

COMPARISON OF CIRBRONZE, CIRCUS AND DIXIE

| CULTIVAR | BRANCHING PATTERN | FLOWERING RESPONSE PERIOD | CAPITULUM FORM AND TYPE |
|---|---|---|---|
| Cirbronze | Semi-spreading | 9 week | Flat Daisy |
| Circus | Semi-spreading | 9 week | Flat Daisy |
| Dixie | Semi-spreading | 9 week | Flat Daisy |

COMPARISONS MADE OF PLANTS GROWN IN A GREENHOUSE IN SALINAS, CALIFORNIA.

We claim:

1. A new and distinct cultivar of *Chrysanthemum morifolium,* Ramat., known by the cultivar name Cirbronze and particularly characterized as to uniqueness by the combined characteristics of daisy capitulum type; flat capitulum form; medium bronze ray floret color, diameter across face of capitulum from 55 to 75 mm. at maturity; uniform nine week flowering response to photoperiodic control; medium plant height; and semi-spreading branching pattern.

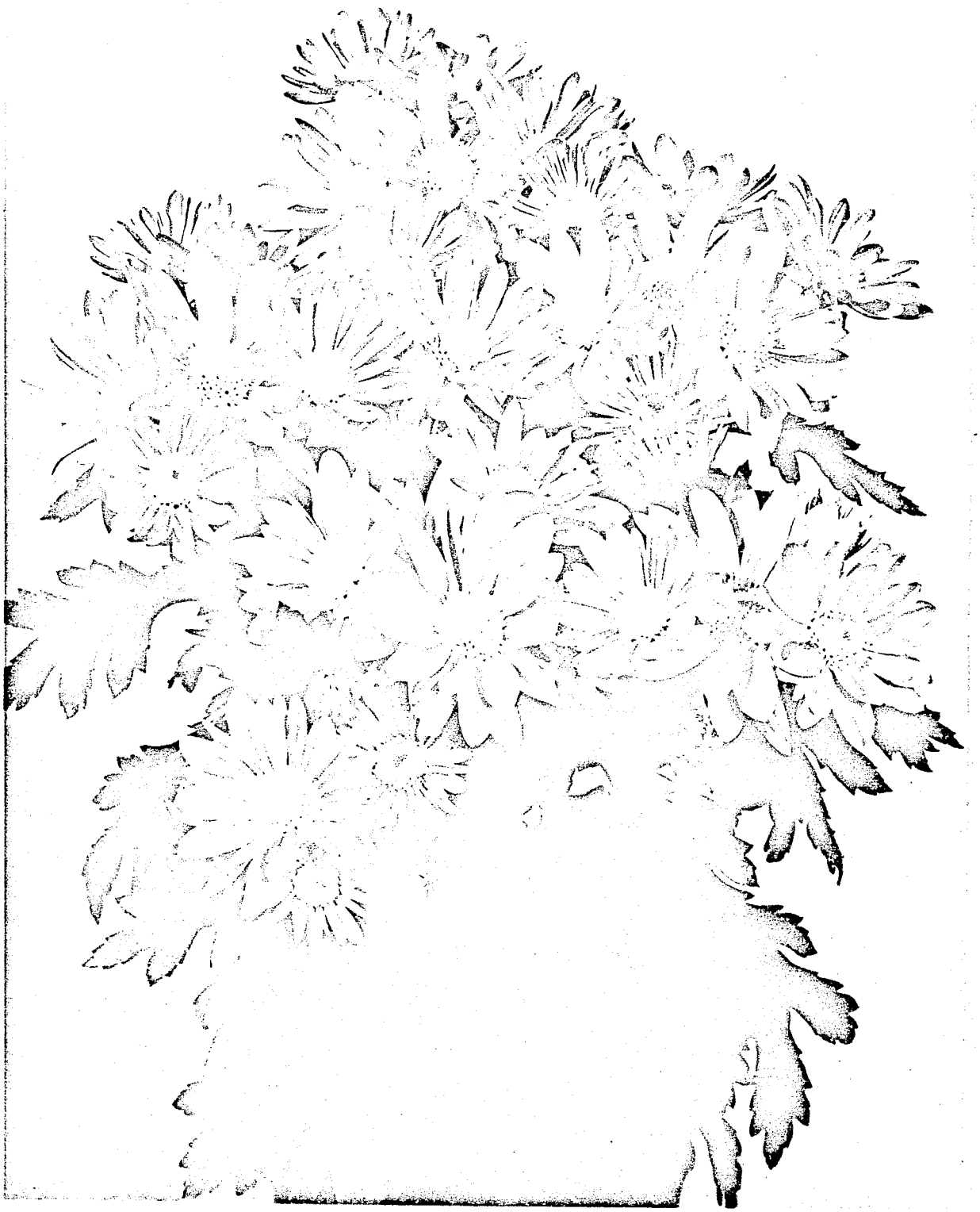

* * * * *